United States Patent [19]

Christensen

[11] Plant 5,156

[45] Dec. 13, 1983

[54] ROSE PLANT CV. AROCHER

[75] Inventor: Jack E. Christensen, Ontario, Calif.

[73] Assignee: Armstrong Nurseries, Inc., Ontario, Calif.

[21] Appl. No.: 390,898

[22] Filed: Jun. 22, 1982

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A hybrid tea having large blooms which turn from pink to dark red.

1 Drawing Figure

This invention relates to a new class of hybrid tea rose cv. Arocher. The plant is a half-hardy to hardy bush type outdoor seedling for garden decoration. It was propagated by Jack E. Christensen in Ontario, Calif., having as its seed parent an undisseminated seedling of "White Satin ×Bewitched" (White Satin is the cultivar of U.S. Plant Pat. No. 2,648 and Bewitched is the cultivar of U.S. Plant Pat. No. 2,755). The pollen parent of Arocher is "Double Delight" (U.S. Plant Pat. No. 3,847). Arocher holds its distinguishing characteristics through succeeding propagations by budding.

The new rose cv. "Arocher" stands apart from other cultivars in that it possesses a unique combination of characteristics; namely: its flower coloration is basically pink, turning to a deep blood red essentially as described and illustrated. The plant provides an abundant quantity of large flowers, often the first rose to open in the spring, and reblooms rapidly throughout the growing season. The profusion of blooms is well distributed over a medium height bush of spreading habit and good vigor. It is well adapted for both individual and mass plantings. Because of its female sterility, it is a low-care plant and does not require the removal of old flowers in order to maintain good bloom production. The wavy leaflet margins of Arocher provide an unusual overall appearance to the semi-glossy foliage.

The new cultivar may be distinguished from its seed parent "White Satin×Bewitched" by the following characteristics:

"White Satin×Bewitched" bears flowers of uniform pink coloration, whereas the new rose cv. Arocher bears flowers that open pink and change to red as described and illustrated hereinafter.

"White Satin×Bewitched" bears flowers on very long strong stems, whereas the Arocher cultivar bears flowers on significantly shorter stems.

The rose cv. Arocher grows as a bush of medium height in an upright spreading habit as described below, whereas the seedling parent grows as a significantly taller bush (about twice the height of the new cultivar) and with a very upright habit.

This new cultivar may be distinguished from its pollen parent, Double Delight, by the following characteristics:

Whereas Double Delight bears flowers that initially are white and then turn pink, flowers of the Arocher variety start pink and then turn red as described.

The flowers of the rose cv. Double Delight have a very strong, penetrating, fruity fragrance, whereas the new cultivar's flowers develop only a moderately spicy fragrance. The flowers of Double Delight have flowers with numerous (i.e., about 160) pistils. The new cultivar bears flowers with significantly fewer (about 65) pistils.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the R.H.S. Colour Chart, published the The Royal Horticultural Society, London, England.

FLOWER

The flowers of the new rose cv. Arocher are usually borne singly (sometimes two or more to a stem). They grow in irregular flat clusters on normal to strong stems of short to medium length. Outdoors, in Ontario, Calif., it yields an abundant quantity of blooms nearly continuously during the growing season. The flowers have a slight to moderate centifolia to spicy fragrance.

BUD

The peduncle is of average length, and average caliper, erect and stiff. It is almost smooth with a few stipitate glands.

Before the calyx breaks, the bud is large in size, of medium-length and ovoid in form, with a few foliaceous appendages and few stipitate glands on the surface of the bud. Usually there are slender foliaceous parts extending beyond the tip of the bud for one-half or more of its length.

As the calyx breaks, the color is near Red, 45A.

The inner surface of the sepals has a fine tomentum lined with stipitate glands.

As the first petal opens, the bud is large in size, medium to long in length, and pointed and ovoid in form. The color of the basal attachment zone is near Yellow, 4B, suffuses to between Red, 54A and Red, 47A; areas exposed to sunlight blush to between Red, 46A and Red, 45A. The inside basal attachment zone is near Yellow, 4B and suffuses to between Red, 46C and Red, 54A with little to no blushing. The bud opens up well and is not prevented from opening by hot, wet or dry weather.

BLOOM

The size of the bloom when fully open is of average to large size ranging from $4\frac{1}{2}$ to $5\frac{1}{2}$ inches. The petalage is very double, with from 35 to 45 petals, plus from 1 to 10 petaloids, arranged regularly. The bloom is full and high centered at first, becoming open to high-centered. At first the petals remain somewhat cupped, with tips reflexed outward and becoming later, at maturity, loosely cupped with tips reflexed outward.

The petals are of a thick, moderately leathery texture with a velvety inside and a shiny to satiny outside. The outside petals are broadly obovate with a flat apex and occasional notches. The intermediate petals are obovate with a flat apex and occasional notches. The inside petals are narrowly obovate with a flat apex and occasional notches. The colors may be modified by being dotted, shaded and/or washed or tinted with other colors.

The paragraphs immediately following describe the color values observed in a flower newly opened in the month of November. The plant had been grown outdoors in Ontario, Calif.

The outer surface of the outside petal showed a basal attachment zone of near Yellow, 4A that suffuses to between Red, 37D and Red, 49A. Areas exposed to sunlight blush to varying red shades as deep as Red, 53C. The inner surface of the outside petal showed a basal attachment zone of near Yellow, 4A that suffuses quickly to between Red, 54A and Red, 55A; areas exposed to sunlight blush to between Red, 45A and Red, 46A.

The outer and inner surfaces of the intermediate petals show the coloration of the outer and inside petals respectively of the above-described outside petals but with less blushing. The inner and outer surfaces show the coloration of the inner and outer petals, intermediate petals but with virtually no blushing.

The paragraph immediately following describes color values observed in a bloom which had been open outdoors for three days, in the month of November. The plant had been grown outdoors in Ontario, Calif.

The outer surface of the basal attachment zone of the petals showed a basal attachment zone of near Yellow, 6C that suffuses to near Red, 49C and with the color intensifying to between Red, 55A and 53A toward the petal edge.

The coloration of the outside surface of the inner petals is the same as that of the outside surface of the outside petals but with slightly less color intensification.

The coloration of the inside surface of the inner petals is the same as that of the outside petals but with less of the area blushed.

The general color effect of the newly opened flower is near Red, 55B for the inner petals and with the outer petals predominantly between Red, 45A and 46A. The bloom after being three days open gives a general color effect which predominantly is between Red, 45A and 46A with occasional hints of color near Red, 55B. The petals drop off cleanly and are not particularly affected by cold, hot, wet or dry weather.

In November, flowers on the bush in the garden persist for 4 to 5 days. Cut roses grown outdoors during November and kept at living-room temperatures will last from 4 to 6 days in the month of November.

REPRODUCTIVE ORGANS

The stamens are average in number and are arranged regularly about the pistils.

The filaments are of medium-length.

The anthers are medium size to large, all opening approximately at once; when immature the coloration is near Yellow-Orange, 15A and when mature, the coloration is near Greyed-Orange, 165A.

Pollen is sparse to moderate and near Yellow-Orange, 15B in color.

There is an average number (approximately 65) of pistils.

The styles are moderately uneven, of short to average length, average caliper and somewhat loosely bunched.

The stigma is near Yellow, 4A in color.

All ovaries are usually enclosed in the calyx.

The plant does not set hips in the Ontario, Calif. climate.

FOLIAGE

The compound leaves usually comprise from three to five leaflets. There is an abundant quantity of such leaves, which are of medium size, somewhat leathery, semi-glossy and with wavy margins. The leaflets vary from round to broadly oval to ovoid in shape, with mucronate apex, and acute base. The margin is simply serrate.

The mature foliage displays upon its upper surface a color which is between Yellow-Green, 147A and Green, 139A. The under surface is near Yellow-Green, 147B.

The young foliage on its upper surface is between Greyed-Purple, 183A and 183B with occasional washes near Yellow-Green, 147B. On its under surface, it is near Greyed-Purple, 183D washed with near Yellow-Green, 147A.

The rachis is of average size, grooved on its upper side, with a few stipitate glands on the edges; the under side being extremely smooth.

The stipules are of medium-length to long, moderately narrow, with medium length points, turning out at an angle of more than 45°.

The plant displays a more than average resistance to mildew and blackspot compared to other commercial varieties grown in the locality named under comparable conditions.

GROWTH

The plant is of upright-bushy spreading habit, and much branched. It displays a very vigorous growth. The canes are of medium to heavy caliper.

The main stems are near Yellow-Green, 146D in color. They bear several large prickles which are of medium length, almost straight but hooked slightly downward and with a medium-length narrow base. The color is near Greyed-Orange, 166B. There are few small prickles (near Greyed-Orange, 166B) and no hairs.

The branches are a color between Yellow-Green, 144A and 146A; the area exposed to the sun blushes with near Greyed-Purple, 183B. They bear several prickles, which are of medium length, almost straight, but hooked slightly downward; with a medium-length, moderately narrow base. The color is near Yellow-Green, 151A and is sometimes blushed with near Greyed-Purple, 183B. There are a few small prickles (of the same coloration as the large prickles) and no hairs.

New shoots are between Greyed-Purple, 183C and 183D in color with washes of near Yellow-Green, 147B. They bear several large prickles, which are of medium length, almost straight but hooked slightly downward and with a medium-length narrow base. The color is near Greyed-Purple, 183B. There are several small prickles (coloration is the same as the large prickles) and no hairs.

I claim:

1. A new and distinct variety of rose plant of the hybrid tea class, substantially as herein shown and described, being particularly characterized in its flower coloration is initially essentially pink and turns to a deep blood red, its large flower size, its abundant production of flowers, and its wavy leaflet margins.

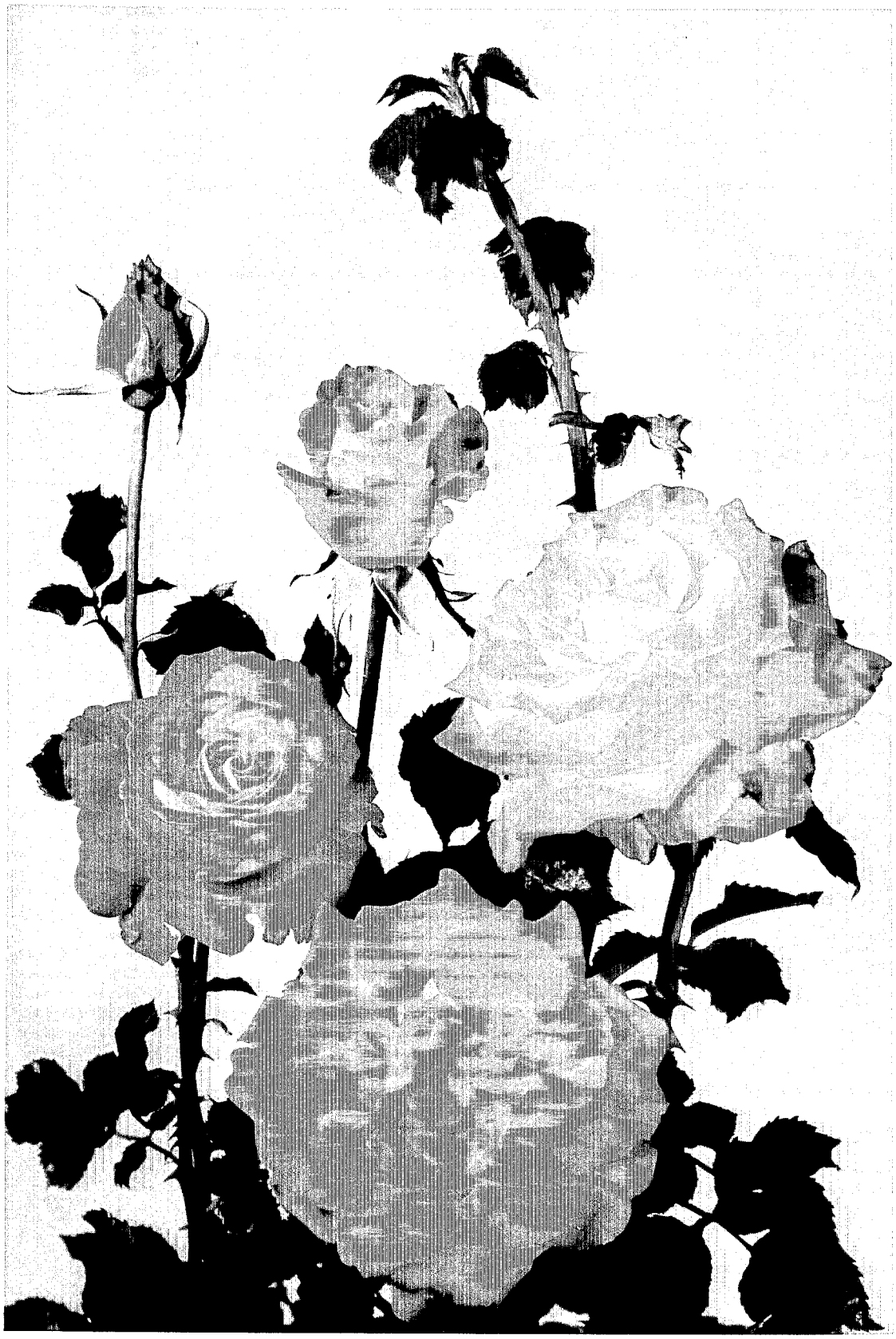

* * * * *